(12) United States Patent
Murai (10) Patent No.: US 7,538,867 B2
(45) Date of Patent: May 26, 2009

(54) MURA DEFECT INSPECTION MASK, APPARATUS AND METHOD OF INSPECTING THE MURA DEFECT, AND METHOD OF PRODUCING A PHOTOMASK

(75) Inventor: Makoto Murai, Kumamoto (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 11/139,970

(22) Filed: May 31, 2005

(65) Prior Publication Data

US 2005/0280805 A1    Dec. 22, 2005

(30) Foreign Application Priority Data

May 28, 2004    (JP)    ............ P.2004-159765

(51) Int. Cl.
*G01N 21/00* (2006.01)

(52) U.S. Cl. ................................. 356/237.5

(58) Field of Classification Search ... 356/237.1–237.5, 356/239.1, 239.3, 600; 430/5, 30
See application file for complete search history.

(56) References Cited

U.S. PATENT DOCUMENTS

| | | | | |
|---|---|---|---|---|
| 5,004,340 A * | 4/1991 | Tullis et al. | ............ | 356/243.6 |
| 5,214,486 A * | 5/1993 | DeWitt | ............ | 356/243.6 |
| 5,585,211 A * | 12/1996 | Firstein et al. | ............ | 430/30 |
| 5,781,657 A * | 7/1998 | Masuda | ............ | 382/147 |
| 5,898,491 A * | 4/1999 | Ishiguro et al. | ............ | 356/243.4 |
| 5,917,935 A * | 6/1999 | Hawthorne et al. | ............ | 382/149 |
| 6,048,649 A * | 4/2000 | Burke et al. | ............ | 430/5 |
| 6,154,561 A * | 11/2000 | Pratt et al. | ............ | 382/141 |
| 6,482,557 B1 * | 11/2002 | Chen et al. | ............ | 430/30 |
| 6,721,695 B1 * | 4/2004 | Chen et al. | ............ | 703/7 |
| 6,876,445 B2 * | 4/2005 | Shibuya et al. | ............ | 356/237.2 |
| 6,973,209 B2 * | 12/2005 | Tanaka | ............ | 382/149 |

(Continued)

FOREIGN PATENT DOCUMENTS

JP    10-300447 A    11/1998

(Continued)

OTHER PUBLICATIONS

Xu et al. "Analysis of defect classification and sizing information with a dedicated white light/laser-confocal microscope review station", Proceedings of SPIE—vol. 3236 pp. 511-514, Feb. 1997.*

(Continued)

*Primary Examiner*—Roy Punnoose
*Assistant Examiner*—Tara S Pajoohi
(74) *Attorney, Agent, or Firm*—Sughrue Mion, PLLC (57) ABSTRACT

Plural repetitive patterns 61 are formed on a transparent substrate 62 in the unit of a chip 65. Each of the repetitive patterns has plural pseudo mura defects 66 to which intensities of mura defects occurring in a predetermined repetitive pattern are allocated with being stepwise changed, for respective kinds of the mura defects.

The mura defects are a CD Mura based on an abnormality in critical dimension of unit patterns 63 in the repetitive patterns, a Pitch Mura based on an abnormality in interval of the repetitive patterns, a Butting Mura based on a positional displacement of the repetitive patterns, and a Defect mura based on a pattern defect of unit patterns in the repetitive patterns.

23 Claims, 9 Drawing Sheets

U.S. PATENT DOCUMENTS

| | | | | |
|---|---|---|---|---|
| 7,126,681 B1 * | 10/2006 | Chen et al. | ............... | 356/237.4 |
| 2002/0150286 A1 * | 10/2002 | Onishi | ........................ | 382/149 |
| 2003/0113007 A1 * | 6/2003 | Iwasaki et al. | .............. | 382/141 |
| 2003/0201410 A1 * | 10/2003 | Nagamura | ............. | 250/559.45 |
| 2005/0264798 A1 * | 12/2005 | Nishiyama et al. | ....... | 356/237.2 |
| 2006/0158642 A1 * | 7/2006 | Tanaka | ................... | 356/237.5 |
| 2006/0203233 A1 * | 9/2006 | Yu | ........................ | 356/237.2 |

FOREIGN PATENT DOCUMENTS

JP      2003-297888 A      10/2003

OTHER PUBLICATIONS

Jerry X. Chen et al., "Universal Inspection Standard for Evaluation of Inspection System and Algorithm Sensitivity and Runability", Proceedings of SPI—vol. 4066 pp. 327-337, 2000.*

* cited by examiner

MURA DEFECT INSPECTION MASK, APPARATUS AND METHOD OF INSPECTING THE MURA DEFECT, AND METHOD OF PRODUCING A PHOTOMASK

The present invention claims foreign priority to Japanese patent application no. P. 2004-159765, filed on May 28, 2004, the contents of which is incorporated herein by reference.

BACKGROUND OF THE INVENTION

1. Field of the Invention

The present invention relates to a method of inspecting a mura defect, an apparatus for inspecting a mura defect, and a method of producing a photomask.

2. Description of the Related Art

A photomask used in pattern formation in a process of producing a semiconductor device, an imaging device, or a display device has a configuration in which a opaque film made of chromium or the like is partly removed away to be formed into a desired pattern on a transparent substrate such as a glass plate.

The photomask is produced in the following method. The opaque film is formed on the transparent substrate, and a resist film is formed on the opaque film. Then, a predetermined pattern is exposed onto the resist film by conducting a writing process using an electron beam or a laser. Thereafter, written portions and unwritten portions are selectively removed away to form a resist pattern. The opaque film is etched with using the resist pattern as a mask, to form an opaque film pattern. Finally, the residual resist is removed away, and a photomask is obtained.

Lithography apparatus which applies a writing process directly to the resist film by means of scanning with the electron beam or the laser are roughly classified into a raster scan system and a vector scan system. In the raster scan system, the beam (the electron beam or the laser) scans over the whole writing area, and, when the beam reaches a pattern portion, the beam is turned ON to draw a pattern. The beam scans in the Y-direction with a constant scan width. When the scanning operation in the Y-direction is ended, the beam is fed in the X-direction. These operations are repeated to scan the whole writing area.

On the other hand, in the vector scan system, in each of plural scanning areas (writing units), a beam scans only over a portion in which a pattern is to be formed. When a scanning operation for one pattern is ended, the beam is turned OFF, and then moved to the next portion in which a pattern is to be formed, in the same scanning area. The beam is again turned ON, and scans over the portion. When all patterns in the scanning area have been written, the beam is moved to the next scanning area by movement of an X-Y table.

When any of the above-described writing systems is employed, writing joints exist due to the beam scan width or the beam diameter, and there arises a problem in that an error due to a writing failure such as a butting error occurring in such joints is periodically caused in each of the writing units.

In a member having a repetitive pattern which is regularly arranged in accordance with a pixel pattern, for example, a photomask for producing an imaging device such as a solid-state imaging device (e.g., a CCD, a CMOS, etc.), a display device such as a liquid crystal display panel, or like image device, particularly, periodic errors, which are caused by a writing failure as described above, occur on a regular repetitive pattern. Even when each of the errors has a size which is so small as to be invisible in micro scale (for example, several tens of nm), the errors resulted in a continuous linear error which could become visible. As a result, a mura defect such as mura in sensitivity or that in display occurs to cause a problem in that the performance of the device is lowered. A regular error which occurs unintentionally in a regularly arranged pattern as in the above example is referred to as "mura defect."

Conventionally, the pattern dimension inspection, the pattern defect inspection, and the particle inspection are usually conducted as inspections for ensuring the quality of a photomask. However, these inspections are conducted for inspecting local defects on a photomask, and hence hardly detect a defect such as the mura defect or a defect which is recognized only in a wide area on the photomask. Therefore, the mura defect is detected by a visual inspection which is subjective inspection.

On the other hand, for example, Japanese Patent Unexamined Publication JP-A-10-300447 discloses an apparatus for inspecting the mura defect in an image device substrate (for example, a TFT liquid crystal substrate). In the apparatus for inspecting a mura defect, the surface of a substrate is illuminated with light, and scattered light from an edge portion of a pattern formed on the surface is observed, thereby detecting the mura defect.

In such a visual inspection of the mura defect, however, inspection results are dispersed depending on the worker conducting the inspection. Because of this reason and the like, the mura defect of the photomask cannot be accurately detected. As a result, there is a problem in that the yield of devices is lowered.

In a device produced with using the photomask, it is considered that the mura defect of the device is caused not only by the photomask but also by other reasons such as stitching exposure of the photomask. In the apparatus for inspecting the mura defect disclosed in the JP-A-10-300447, it is difficult to identify the cause of a detected mura defect.

Furthermore, there are various kinds of mura defects in which shapes and regularities are different depending on, for example, the cause of occurrence. However, the apparatus for inspecting the mura defect disclosed the JP-A-10-300447 cannot accurately detect plural kinds of mura defects which are required to be inspected.

The present invention has been conducted in view of the above-discussed circumstances. It is one of the objects of the present invention to provide the mura defect inspection mask which is useful in accurate detection of the mura defect occurring in a repetitive pattern of a member to be inspected.

It is one of other objects of the present invention to provide an apparatus for inspecting the mura defect which can accurately detect the mura defect occurring in a repetitive pattern of a member to be inspected.

Further, it is one of other objects of the present invention to provide a method of inspecting the mura defect which can accurately detect the mura defect occurring in a repetitive pattern of a member to be inspected and a method of producing a photomask in which the mura defect occurring in a repetitive pattern of the photomask can be accurately detected.

The apparatus for inspecting the mura defect disclosed in the JP-A-10-300447 can detect the mura defect. However, the apparatus cannot qualitatively evaluate the mura defect, and, for example, cannot differentiate the mura defect which requires an inspection from that which does not require an inspection, or quantitatively evaluate a mura defect on the basis of the intensity of the defect.

SUMMARY OF THE INVENTION

The present invention has been achieved in view of the above-discussed circumstances. One of the objects of the present invention is to provide a method of inspecting a mura defect in which a mura defect occurring in a repetitive pattern of a member to be inspected can be evaluated qualitatively and quantitatively, and the mura defect can be accurately detected.

It is one of other objects of the present invention to provide an apparatus for inspecting the mura defect which can evaluate qualitatively and quantitatively the mura defect occurring in the repetitive pattern of the member to be inspected, and accurately detect the mura defect.

It is one of further objects of the present invention to provide a method of producing a photomask which enables the mura defect occurring in a repetitive pattern of a photomask to be evaluated qualitatively and quantitatively, and detected accurately.

According to a first aspect of the present invention, there is provided a mura defect inspection mask, comprising:
  a transparent substrate; and
  an opaque film formed on the substrate,
  wherein plural repetitive patterns are formed by the opaque film on the substrate,
  wherein each of the repetitive patterns has plural pseudo mura defects,
  wherein intensities of the pseudo mura defects vary in a stepwise manner among the repetitive patterns.

According to a second aspect as set forth in the first aspect of the present invention, it is preferable that the kinds of the mura defects are at least one of a CD Mura; a mura defect based on an abnormality in critical dimension of unit patterns in the repetitive patterns, a Pitch Mura; a mura defect based on an abnormality in interval of the unit patterns in the repetitive patterns, a Butting Mura; a mura defect based on a positional displacement of the unit patterns in the repetitive patterns, and a Defect Mura; a mura defect based on a pattern defect of the unit patterns in the repetitive patterns.

According to a third aspect of the present invention, there is provided an apparatus for inspecting a mura defect which inspects a mura defect occurring in a repetitive pattern of a member to be inspected, the repetitive pattern having a large number of unit patterns that are regularly arranged, the apparatus comprising:
  a light source;
  a stage on which the member to be inspected is placed;
  a light receiving unit receiving the light affected by the member to be inspected; and
  an analyzing unit analyzing the mura defect in accordance with the light affected detected by the light receiving unit,
  wherein the apparatus is calibrated so that a detection sensitivity is ascertained or calibrated by detecting plural pseudo mura defects of the mura defect inspection mask according to the first aspect of the present invention.

According to a fourth aspect as set forth in the third aspect of the present invention, it is preferable that the member to be inspected is an image device, or a photomask for producing the image device.

According to a fifth aspect of the present invention, there is provided a method of inspecting the mura defect in which the mura defect occurring in a repetitive pattern of a member to be inspected is inspected, the repetitive pattern having a large number of unit patterns that are regularly arranged, the method comprising the steps of:
  irradiating light onto the member to be inspected;
  receiving affected light from the member to be inspected; and
  inspecting the mura defect of the repetition patter on the member to be inspected using an apparatus for inspecting a mura defect,
  wherein the apparatus for inspecting the mura defect comprises:
  a light source;
  a stage on which the member to be inspected is placed;
  a light receiving unit receiving the light affected by the member to be inspected; and
  an analyzing unit analyzing the mura defect in accordance with the light affected detected by the light receiving unit,
  wherein the apparatus is calibrated so that detection sensitivity is ascertained or calibrated by detecting plural pseudo mura defects of a mura defect inspection mask, the mura defect inspection mask comprising:
    a transparent substrate; and
    an opaque film formed on the substrate,
    wherein plural repetitive patterns are formed by the opaque film on the substrate, each of the repetitive patterns having plural pseudo mura defects to which intensities of mura defects occurring in a predetermined repetitive pattern are allocated with being stepwise changed, for respective kinds of the mura defects.

Note that the light receiver may receive the light reflected or transmitted light from the member to be inspected.

According to a sixth aspect as set forth in the fifth aspect of the present invention, it is preferable that the member to be inspected is an image device, or a photomask for producing the image device.

According to a seventh aspect as set forth in the fifth aspect of the present invention, it is preferable that the method is used for manufacturing a photomask having a predetermined opaque film pattern on a transparent substrate,
  wherein the opaque film pattern is configured by a repetitive pattern in which a large number of unit patterns are regularly arranged.

According to the present invention, plural pseudo mura defects of the mura defect inspection mask are detected, whereby the detection sensitivity is ascertained or calibrated. Therefore, the apparatus for inspecting the mura defect is surely set to a detection sensitivity which is set in a mura defect inspection mask for each of pseudo mura defect, and at which plural different-intensity pseudo mura defects can be detected. Consequently, the mura defect occurring in a repetitive pattern in a member to be inspected or a photomask can be accurately detected.

DETAILED DESCRIPTION OF THE PREFERRED EMBODIMENTS

Hereinafter, the best mode for carrying out the present invention will be described with reference to the accompanying writings.

Figure 1:
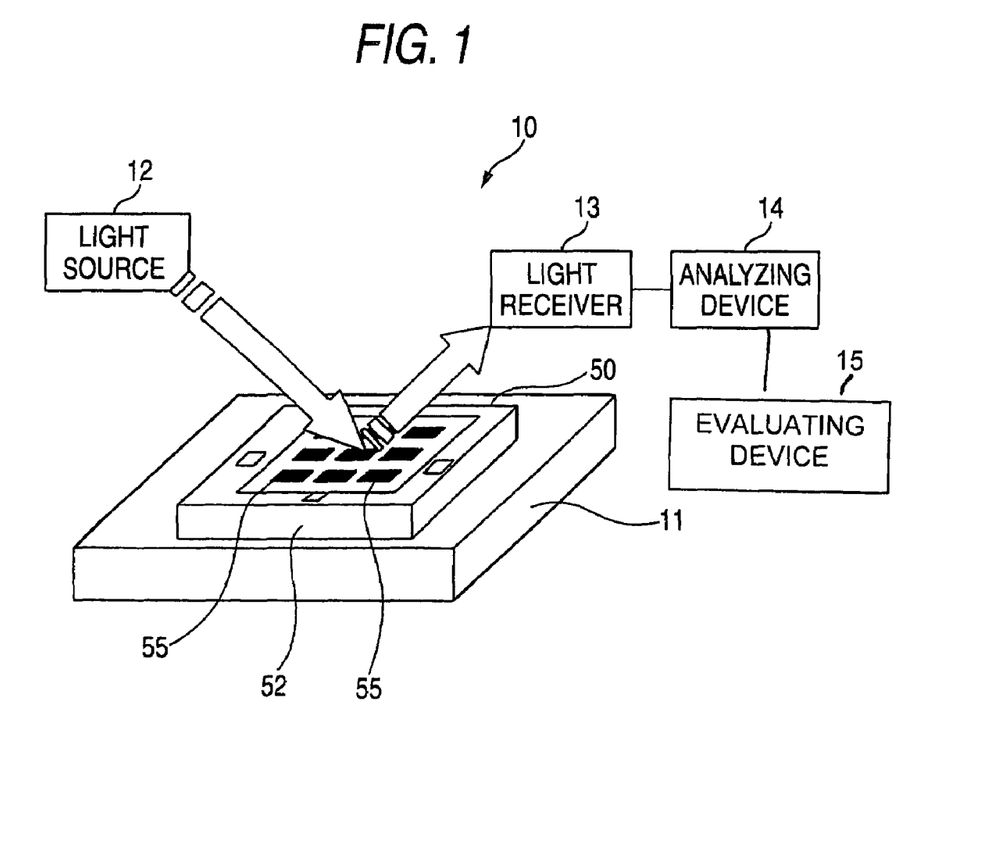
FIG. 1 is a perspective view showing the configuration of an embodiment of the apparatus for inspecting the mura defect according to the present invention.
Figure 2:
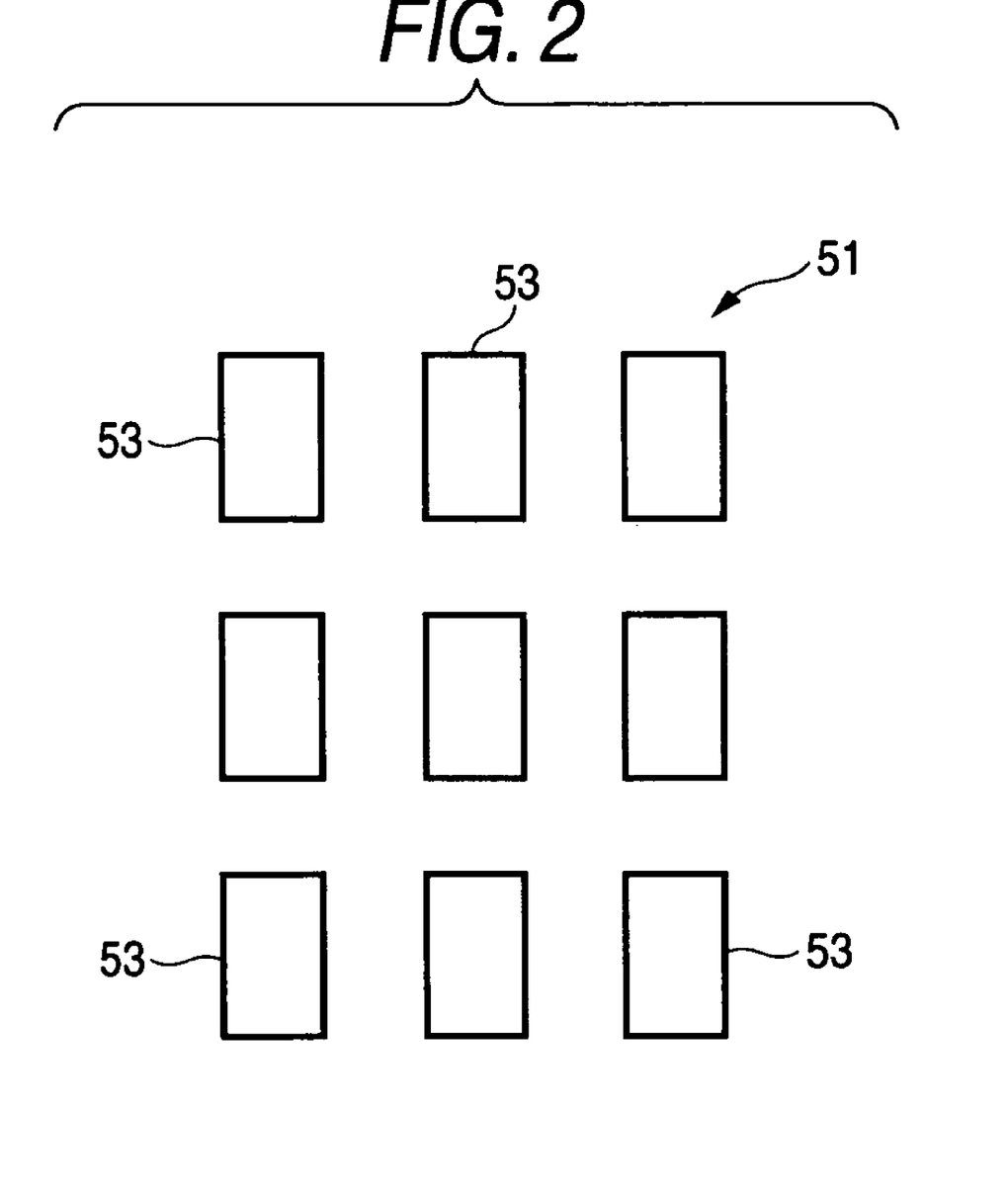
FIG. 2 is a plan view showing a repetitive pattern in a chip of a photomask in FIG. 1.

FIG. 1 is a perspective view showing the configuration of an embodiment of an apparatus for inspecting a mura defect according to the present invention, and FIG. 2 is a plan view showing a repetitive pattern in a chip of a photomask in FIG. 1.

The mura defect inspecting apparatus 10 shown in FIG. 1 detects the mura defect occurring in a repetitive pattern 51 (FIG. 2) formed on the surface of a photomask 50 which is a member to be inspected, and is configured by a stage 11, a light source 12, a light receiver 13, and an analyzing device 14. The photomask 50 is an exposure mask for producing a image device.

The image device is a device in which many pixel patterns are finally subjected to image processing or image display. Examples of such a device are an imaging device and a display device. Typical examples of the imaging device are solid state imaging devices such as a CCD, a CMOS, and a VMIS, and those of a display device are a liquid crystal display device, a plasma display device, an EL display device, an LED display device, and a DMD display device. Specifically, therefore, the pixel pattern forming an imaging face of an imaging device is a repetitive pattern forming light receiving portions of a CCD, a CMOS, or the like, and that forming a displaying face of a display device is a repetitive pattern of, for example, thin film transistors, an opposing substrate, or a color filter of a liquid crystal display device.

In the photomask 50, a opaque film made of chromium or the like is disposed on a transparent substrate 52 made of glass or the like, and the opaque film is partly removed away by the desired repetitive pattern 51 (FIG. 2). The repetitive pattern 51 is used in transferring of the many pixel pattern of the image device by the lithography method, and configured by regularly arranging unit patterns 53 in accordance with the pixel patterns. The reference numeral 55 in FIG. 1 denotes chips configured by forming the repetitive pattern 51. The chips are disposed in the number of about 5×5 in the photomask 50.

A method of producing the photomask 50 has: an opaque film pattern forming step of forming a opaque film pattern formed by the repetitive pattern 51 in which the many unit patterns 53 are regularly arranged; and the mura defect inspecting step of implementing the mura defect inspecting method with using the mura defect inspecting apparatus 10, to inspect the mura defect occurring in the repetitive pattern 51.

In the opaque film pattern forming step, first, the opaque film is formed on the transparent substrate 52, and a resist film is formed on the opaque film. Next, a writing process is applied to the resist film by irradiating the film with an electron beam or a laser beam of a writing apparatus, thereby exposing the resist film a predetermined pattern. Then, written portions or unwritten portions are selectively removed away to form a resist pattern. Thereafter, the opaque film is etched with using the resist pattern as a mask, to form the repetitive pattern 51 which is configured by the many unit patterns 53. As a result, the opaque film pattern is formed.

In the opaque film pattern forming step, when the writing process is applied to the resist film by the scanning of an electron beam or a laser beam, there is a case where joints due to the beam scan width or the beam diameter occur in the writing, and an error due to a writing failure may be periodically caused in each of the writing units. This causes the occurrence of the mura defect. Typical examples of such the mura defect are a CD Mura, a Pitch Mura, a Butting Mura, and a Defect Mura.

Figure 3A:
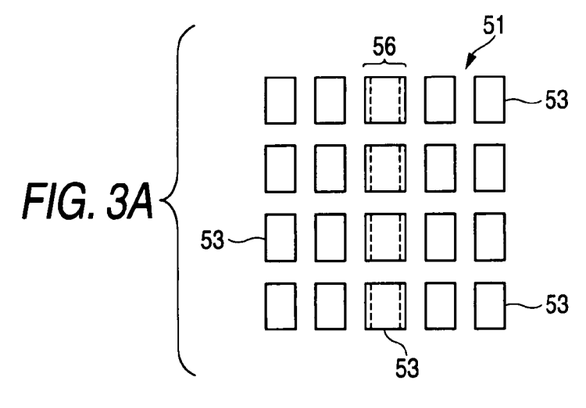
FIGS. 3A to 3D are plan views showing mura defects (CD Muras (3A, 3B) and Pitch Muras (3C, 3D)) occurring in the repetitive pattern of FIG. 2.
Figure 3B:
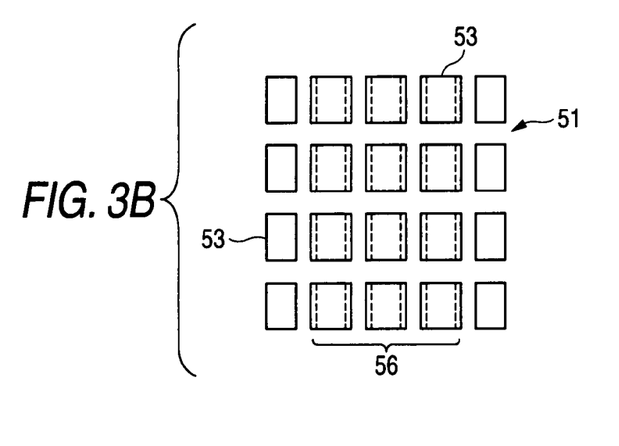

As shown in FIGS. 3A and 3B, a CD Mura 56 is based on an abnormality in critical dimension of the unit patterns 53 in the repetitive pattern 51, and caused by a phenomenon that the unit patterns 53 are thinned or thickened by variation of the beam strength of the writing apparatus.

Figure 3C:
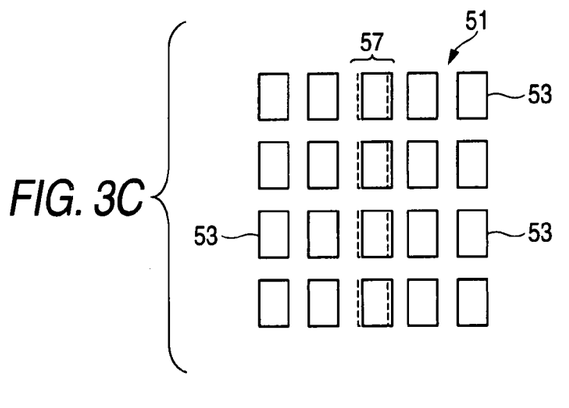
Figure 3D:
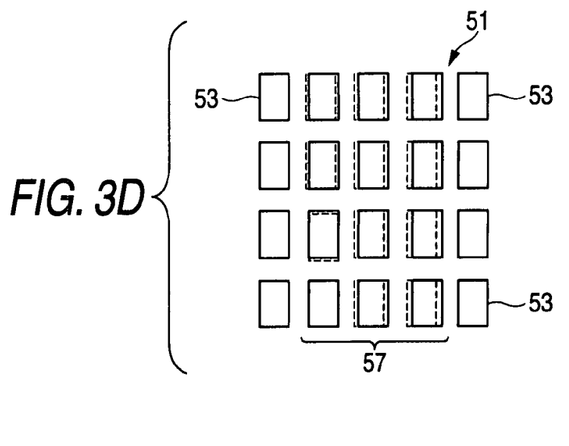

As shown in FIGS. 3C and 3D, a Pitch Mura 57 is based on an abnormality in arrangement interval of the unit patterns 53 in the repetitive pattern 51, and caused by a phenomenon that a positional displacement in a joint of writings occurs and hence the intervals of the unit patterns 53 in the repetitive pattern 51 partly differ.

Figure 4A:
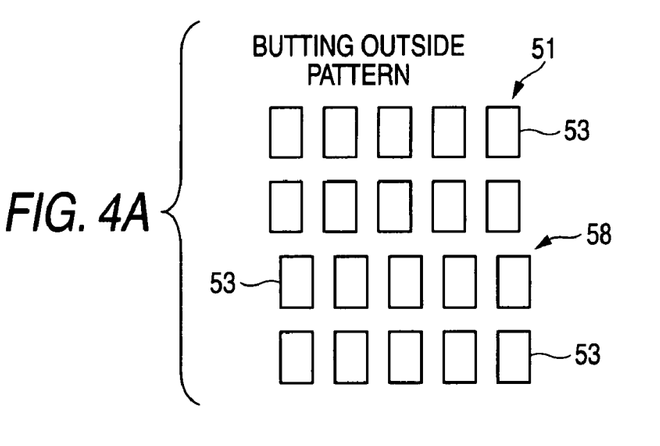
FIGS. 4A to 4D are plan view showing mura defects (Butting Muras (4A, 4B) and Defect Muras (4C, 4D)) occurring in the repetitive pattern of FIG. 2.
Figure 4B:
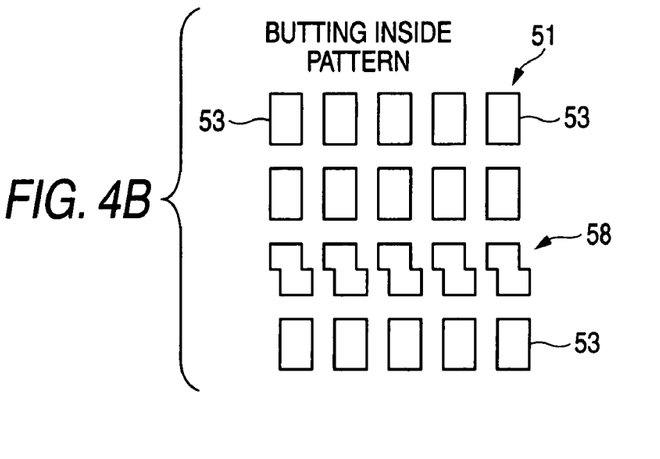

As shown in FIGS. 4A and 4B, a Butting Mura 58 is based on a positional displacement of the unit patterns 53 in the repetitive pattern 51. The Butting Mura 58 is the mura defect (outside pattern Butting Mura) caused by a phenomenon that the position of a certain unit pattern 53 in the repetitive pattern 51 is deviated with respect to another unit pattern 53 by occurrence of a positional displacement in a joint of beam writings, or the mura defect (inside pattern Butting Mura) caused by a phenomenon that deviation occurs in an identical unit pattern 53.

Figure 4C:
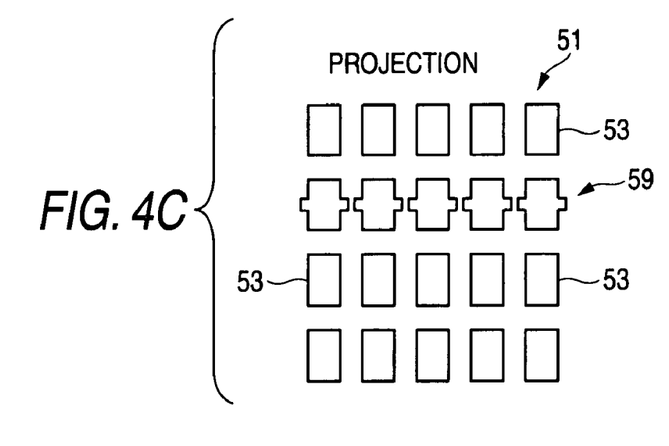
Figure 4D:
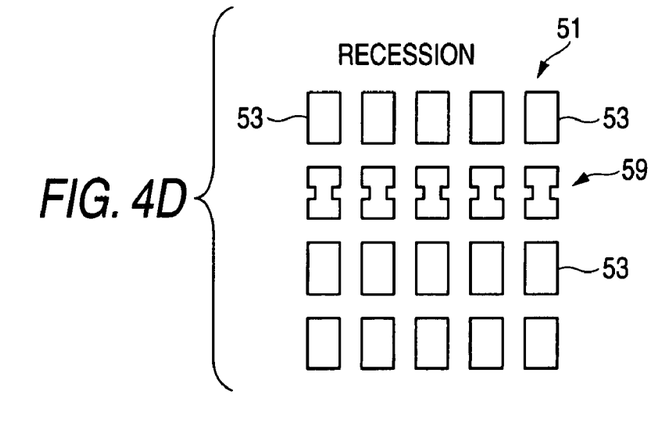

As shown in FIGS. 4C and 4D, a Defect Mura 59 is based on a pattern defect of the unit patterns 53 in the repetitive pattern 51, and is the mura defect (projection) caused by a phenomenon that the unit patterns 53 exist in joints of beam writings and the joints overlap with each other to cause overexposure, or the mura defect (recession) caused by a phenomenon that joints are separated from each other to cause underexposure.

The mura defect inspecting apparatus 10 shown in FIG. 1 detects the above-mentioned four typical mura defects (the CD Mura 56, the Pitch Mura 57, the Butting Mura 58, and the Defect Mura 59) which are required to be detected. The stage 11 of the mura defect inspecting apparatus 10 is a stage on which the photomask 50 is to be placed. The light source 12 is placed above one side of the stage 11, and illuminates the repetitive pattern 51 on the surface of the photomask 50 from an obliquely upper side.

The light receiver 13 is placed above the other side of the stage 11, receives reflected light from the repetitive pattern 51 of the photomask 50, particularly, scattered light from edge portions of the unit patterns 53 of the repetitive pattern 51, and converts the light to received-light data. For example, an imaging sensor such as a CCD line sensor or a CCD area sensor is used as the light receiver 13. When the mura defect occurs in the repetitive pattern 51 of the photomask 50, disturbance in regularity is caused in the received-light data converted by the light receiver. The analyzing device 14 analyzes the received-light data to produce mura defect detection data, and detects the mura defect.

In the mura defect inspecting step of the method of producing the photomask 50, the light source 12 of the mura defect inspecting apparatus 10 illuminates the repetitive pattern 51 of the photomask 50. The light receiver 13 receives light scattered by edge portions of the unit patterns 53 of the repetitive pattern 51. The analyzing device 14 analyzes the received-light data to detect the mura defect. The evaluating device 15 implements the mura defect inspecting method using the mura defect inspecting apparatus 10 in which the evaluating device 15 evaluates the mura defect as described later, thereby inspecting (detecting) the mura defect occurring in the repetitive pattern 51 of the photomask 50.

Figure 6A:
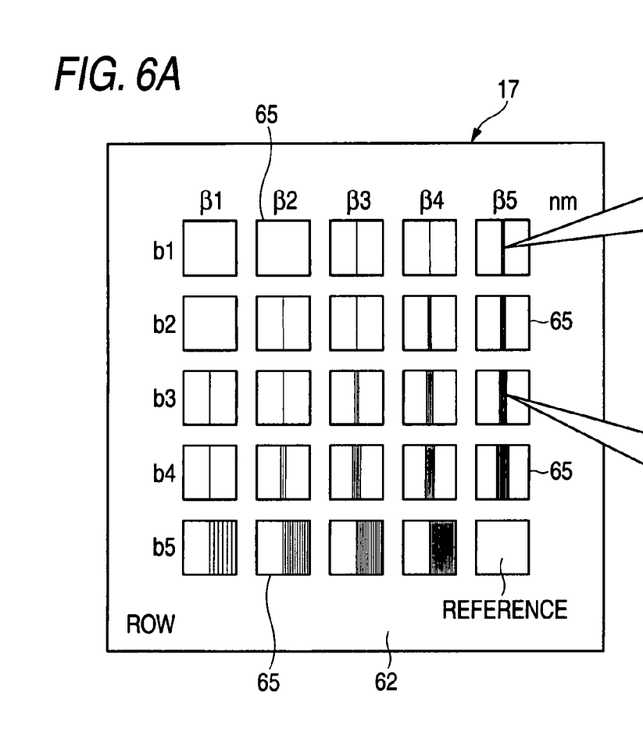
FIGS. 6A to 6C are front views showing a Pitch Mura inspection mask used in the mura defect inspecting apparatus of FIG. 1.
Figure 6B:
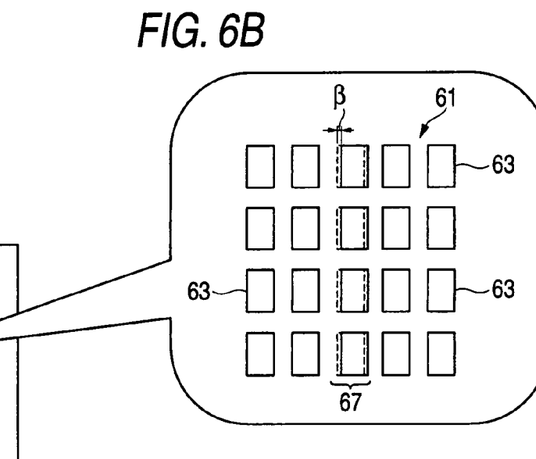
Figure 6C:
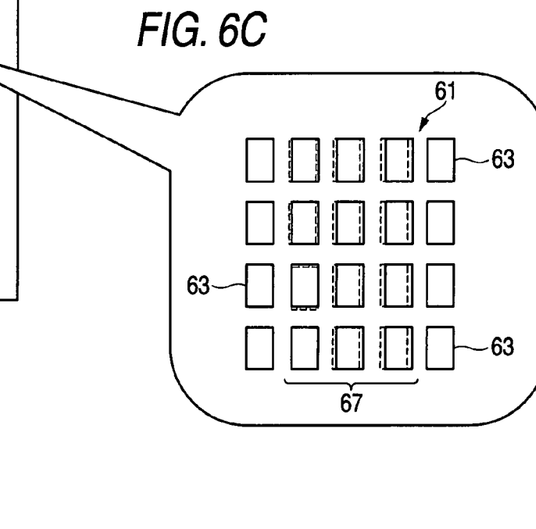
Figure 7A:
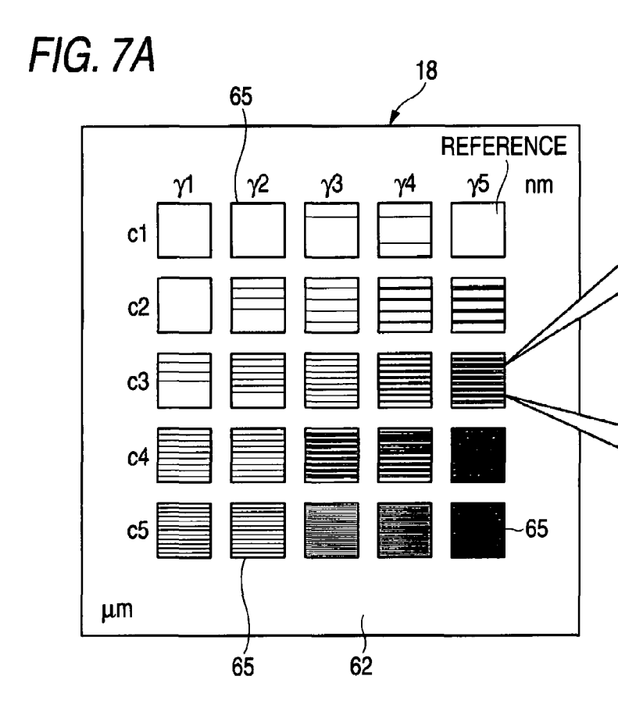
FIGS. 7A to 7C are front views showing a Butting Mura inspection mask used in the mura defect inspecting apparatus of FIG. 1.
Figure 7B:
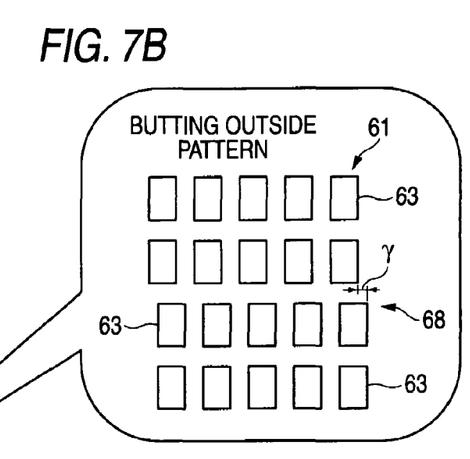
Figure 7C:
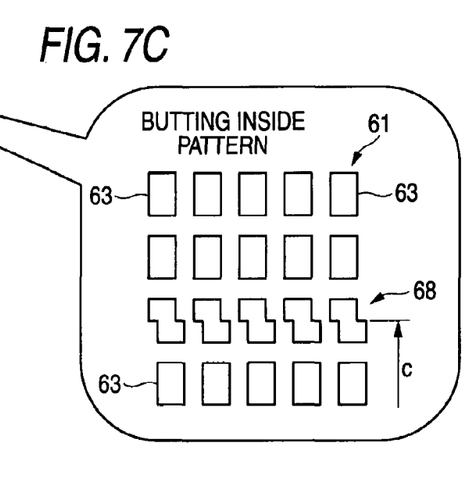
Figure 8A:
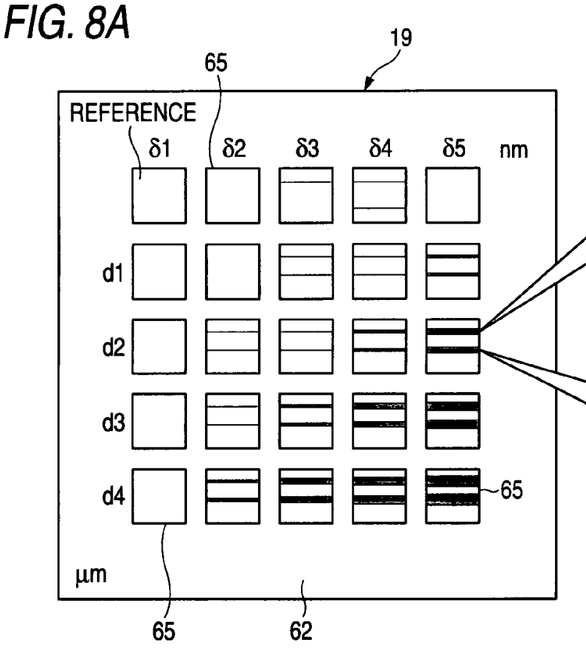
FIGS. 8A to 8C are front views showing a Defect Mura inspection mask used in the mura defect inspecting apparatus of FIG. 1.
Figure 8B:
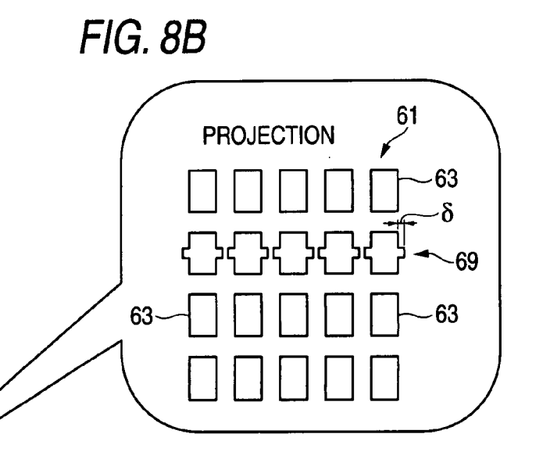
Figure 8C:
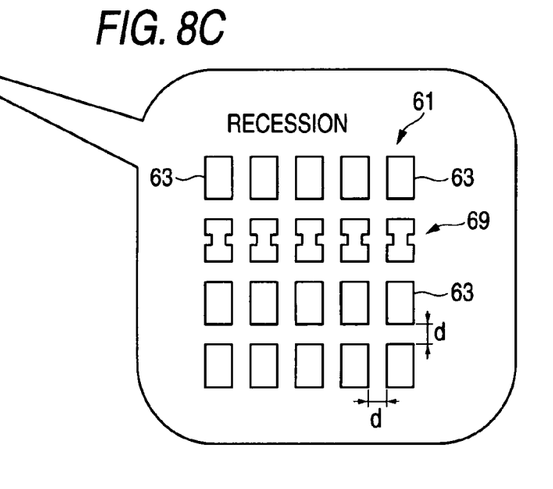
Figure 9A:
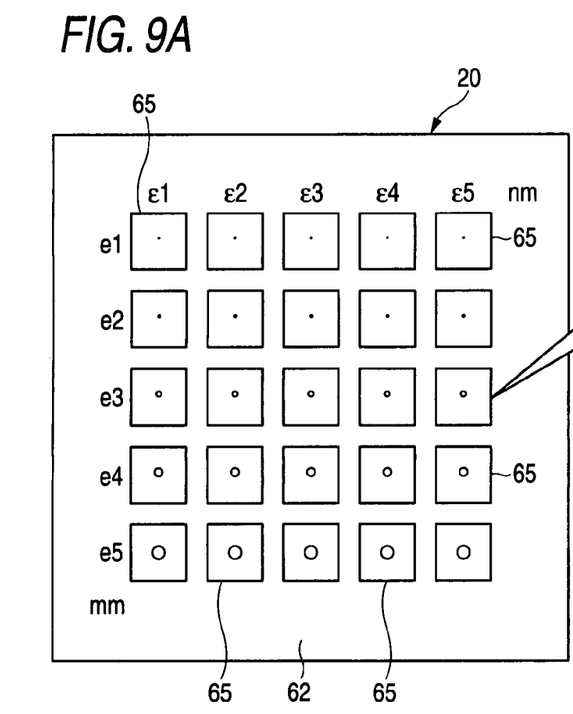
FIGS. 9A to 9D are front views showing a CD Mura inspection mask used in the mura defect inspecting apparatus of FIG. 1.
Figure 9B:
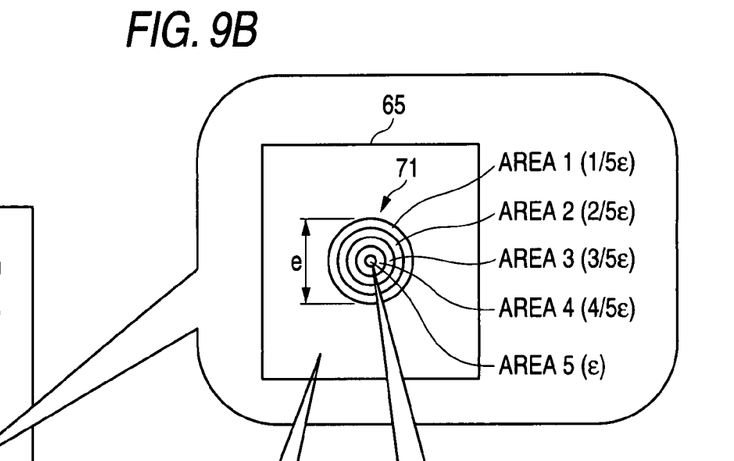
Figure 9C:
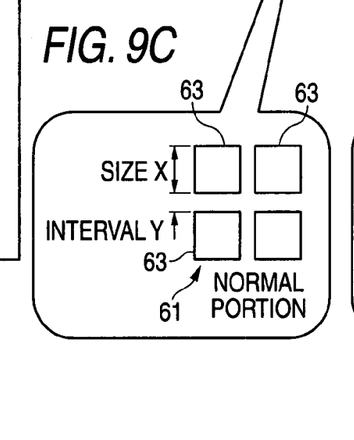
Figure 9D:
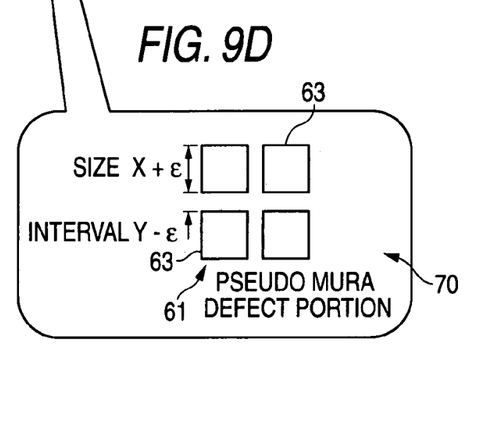

The detection sensitivity of the mura defect inspecting apparatus 10, which is determined by the light receiver 13 and the analyzing device 14, is ascertained whether it is adequate or not, by detecting pseudo mura defects 66, 67, 68, 69 in mura defect inspection masks 16, 17, 18, 19 shown in FIGS. 5 to 8 by the mura defect inspecting apparatus 10. When the detection sensitivity is not adequate, the detection sensitivity is adjusted after the ascertainment so as to be adequate. The mura defect inspection masks are a CD Mura inspection mask 16 (FIG. 5), a Pitch Mura inspection mask 17 (FIG. 6), a Butting Mura inspection mask 18 (FIG. 7), and a Defect Mura inspection mask 19 (FIG. 8).

Each of the mura defect inspection masks 16, 17, 18, 19 is configured by forming chips 65 on a transparent substrate 62. In the chips 65, for each of kinds of mura defects which may occur in predetermined repetitive patterns, plural repetitive patterns 61 each has plural pseudo mura defects 66, 67, 68, or 69, and the intensities of the mura defects vary in a stepwise manner among the repetitive patterns. The repetitive patterns 61 are formed in a opaque film made of chromium of the like on the transparent substrate 62.

Figure 5A:
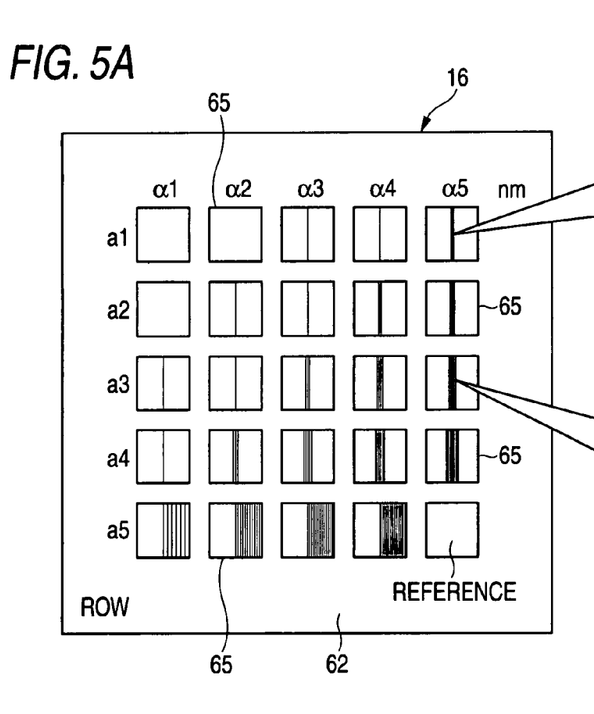
FIGS. 5A to 5C are front views showing a CD Mura inspection mask used in the mura defect inspecting apparatus of FIG. 1.
Figure 5B:
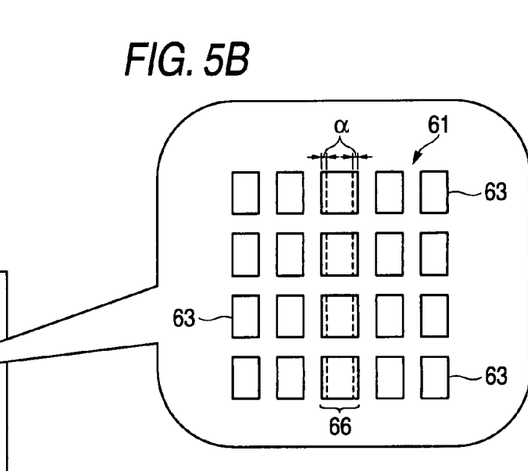
Figure 5C:
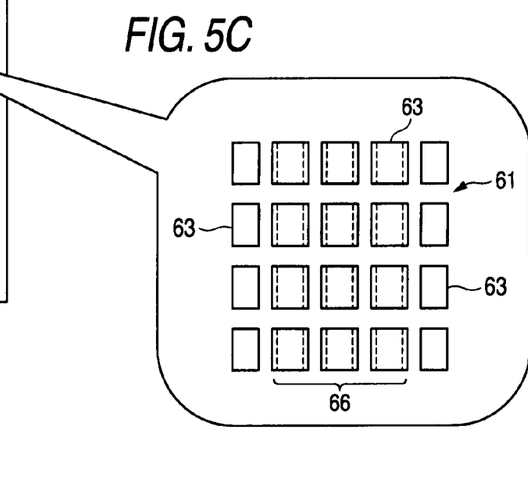

The CD Mura inspection mask 16 shown in FIG. 5 is the mura defect inspection mask in which the CD Mura 56 that is shown in FIGS. 3A and 3B and required to be detected is produced in a pseudo manner. In the CD Mura inspection mask 16, plural chips 65 each comprising a repetitive pattern 61 in which many unit patterns 63 are arranged are transversally and longitudinally placed on the transparent substrate 62. The pseudo mura defects 66 in which the change amounts $\alpha$ in critical dimension of the unit patterns 63 in the repetitive patterns 61 are varied (widened) respectively to $\alpha1$, $\alpha2$, $\alpha3$, $\alpha4$, and $\alpha5$ ($\alpha1<\alpha2<\alpha3<\alpha4<\alpha5$, unit: nm) are inserted in the chips 65 which are transversally placed.

The pseudo mura defects 66 in which the number of insertion rows (insertion areas) is stepwisely changed (increased) to a1, a2, a3, a4, and a5 (a1<a2<a3<a4<a5) are inserted in the chips 65 which are longitudinally placed. Because of the differences of the sizes $\alpha1$, $\alpha2$, $\alpha3$, $\alpha4$, and $\alpha5$ and numbers of the insertion rows a1, a2, a3, a4, and a5 of the pseudo mura defects 66, the intensities of the pseudo mura defects 66 in the CD Mura inspection mask 16 vary in a stepwise manner among the repetitive patterns 61. For example, the chips 65 are shaped as squares, and the pseudo mura defects 66 occupy one third or one half of the squares of the chips 65 in the insertion row a5.

The Pitch Mura inspection mask 17 shown in FIG. 6 is the mura defect inspection mask in which the Pitch Mura 57 that is shown in FIGS. 3C and 3D and required to be detected is produced in a pseudo manner. In the Pitch Mura inspection mask 17 also, plural chips 65 each comprising a repetitive pattern 61, in which many unit patterns 63 are arranged, are transversally and longitudinally placed on the transparent substrate 62. The pseudo mura defects 67 in which the arrangement interval deviation amounts $\beta$ of the unit patterns 63 in the repetitive patterns 61 are stepwisely varied respectively by $\beta1$, $\beta2$, $\beta3$, $\beta4$, and $\beta5$ ($\beta1<\beta2<\beta3<\beta4<\beta5$, unit: nm) are inserted in the chips 65 which are transversally placed.

The pseudo mura defects 67 in which the number of insertion rows (insertion areas) is stepwisely changed (increased) to b1, b2, b3, b4, and b5 (b1<b2<b3<b4<b5) are inserted in the chips 65 which are longitudinally placed. Because of the differences of the sizes $\beta1$, $\beta2$, $\beta3$, $\beta4$, and $\beta5$ and insertion row numbers b1, b2, b3, b4, and b5 of the pseudo mura defects 67, the intensities of the pseudo mura defects 67 in the Pitch Mura inspection mask 17 vary in a stepwise manner among the repetitive patterns 61. For example, the chips 65 are shaped as squares, and the pseudo mura defects 67 occupy one third or one half of the squares of the chips 65 in the insertion row b5.

The Butting Mura inspection mask 18 shown in FIG. 7 is the mura defect inspection mask in which the Butting Mura 58 that is shown in FIGS. 4A and 4B and required to be detected is produced in a pseudo manner. In the Butting Mura inspection mask 18 also, plural chips 65 each comprising a repetitive pattern 61, in which many unit patterns 63 are arranged, are transversally and longitudinally placed on the transparent substrate 62. The outside pattern butting pseudo mura defects 68 are inserted in the upper half of each chip 65, and the inside pattern butting pseudo mura defects 68 are inserted in the lower half of each chip 65. For each of the outside and inside pseudo mura defects 68, the pseudo mura defects 68 in which the positional displacement amounts $\gamma$ of the unit patterns 63 in the repetitive patterns 61 are stepwisely varied respectively to $\gamma1$, $\gamma2$, $\gamma3$, $\gamma4$, and $\gamma5$ ($\gamma1<\gamma2<\gamma3<\gamma4<\gamma5$, unit: nm) are inserted in the chips 65 which are transversally placed.

The outside and inside pseudo mura defects 68 in which the period c of insertion into the repetitive patterns 61 is stepwisely changed (the intervals between pseudo mura defects are decrease) to c1, c2, c3, c4, and c5 (c1<c2<c3<c4<c5) are inserted in the chips 65 which are longitudinally placed. Because of the differences of the sizes $\gamma1$, $\gamma2$, $\gamma3$, $\gamma4$, and $\gamma5$ and insertion periods c1, c2, c3, c4, and c5 pseudo mura defects 68, the intensities of the pseudo mura defects 68 in the Butting Mura inspection mask 18 vary in a stepwise manner among the repetitive patterns 61.

The Defect Mura inspection mask 19 shown in FIG. 8 is the mura defect inspection mask in which the Defect Mura 59 that is shown in FIGS. 4C and 4D and required to be detected is produced in a pseudo manner. In the Defect Mura inspection mask 19 also, plural chips 65 each comprising a repetitive pattern 61 in which many unit patterns 63 are arranged are transversally and longitudinally placed on the transparent substrate 62. Two rows respectively having projections and recessions which are pattern defects of the unit patterns 63 are transversally inserted in each chip 65. The pseudo mura defects 69 in which the size $\delta$ of each of the projections and the recessions are stepwisely varied (increased) respectively by $\delta1$, $\delta2$, $\delta3$, $\delta4$, and $\delta5$ ($\delta1<\delta2<\delta3<\delta4<\delta5$, unit: nm) are inserted in the chips 65 which are transversally placed.

In consideration that the reflectivity affects the Defect Mura 59, the interval d of the unit patterns 63 is set to be stepwisely changed (reduced) to d1, d2, d3, and d4 (d1>d2>d3>d4, unit: μm), in the chips 65 which are longitudinally placed. Because of the difference of the sizes $\delta1$, $\delta2$, $\delta3$, $\delta4$, and $\delta5$ of the projections and the recessions in the pseudo mura defects 69, and those of the distance d1, d2, d3, and d4 in the unit patterns 63, the intensities of the pseudo mura defects 69 in the Defect Mura inspection mask 19 vary in a stepwise manner among the repetitive patterns 61.

In the thus configured embodiment, the mura defect inspecting apparatus 10 detects the plural pseudo mura defects 66, 67, 68, 69 in the mura defect inspection masks 16, 17, 18, 19, whereby the detection sensitivity is ascertained or calibrated. Therefore, the mura defect inspecting apparatus 10 is set to a detection sensitivity at which the respective plural pseudo mura defects 66, 67, 68, 69 in the mura defect inspection masks 16, 17, 18, 19 can be surely detected. Consequently, the mura defect (the CD Mura 56, the Pitch Mura 57, the Butting Mura 58, or the defect mura defect 59) occurring in the repetitive pattern 51 of the photomask 50 can be accurately detected.

The above-described mura defect inspection masks have pseudo mura defects which simulate the mura defects occurring mainly by a writing failure. Mura defect inspection masks which simulate CD Muras due to development of the resist and etching of the opaque film may be added.

The CD Muras due to development of the resist and etching of the opaque film are caused mainly by phenomenon that, for example, the wettability of a processed substrate with respect to a developer and an etchant is partly different, and a CD error occurs in the portion.

The CD Mura inspection mask 20 shown in FIG. 9 is the mura defect inspection mask in which a CD error due to development of the resist and etching of the opaque film is produced in a pseudo manner. In the CD Mura inspection mask 20 also, plural chips 65 comprising a repetitive pattern 61 in which many unit patterns 63 are arranged are transversally and longitudinally placed on the transparent substrate 62.

A pseudo mura defect 70 is inserted in each of the chips 65 which are transversally arranged. The pseudo mura defect 70 is produced in a middle circular area 71 in a pattern 61. In the circular area 71, the dimension X (i.e., the line width) of a unit pattern 63 is changed without changing the center position of the unit pattern 63, and the total change amount $\epsilon$ of the line width is varied by $\epsilon1$, $\epsilon2$, $\epsilon3$, $\epsilon4$, and $\epsilon5$ ($\epsilon1 < \epsilon2 < \epsilon3 < \epsilon4 < \epsilon5$, unit: nm). The circular area 71 has five areas (area 1 to area 5) which are formed by equally dividing into five parts in the radial direction. The line width is changed so that the width change amount is stepwise increased by an equal distance from area 1 toward area 5, and the greatest change amount (the change amount of area 5) is equal to the total change amount $\epsilon$.

The diameter e of the circular area 71 is set to e1, e2, e3, e4, and e5 (e1<e2<e3<e4<e5) with being stepwisely changed (increased), in the chips 65 which are longitudinally placed. Because of the difference of the width change amounts in the circular areas 71 for causing the pseudo mura defects 70 in the repetitive patterns 61, and that of the sizes (diameters e) of the circular areas 71, the intensities of the pseudo mura defects 67 in the CD Mura inspection mask 20 vary in a stepwise manner among the repetitive patterns 61.

In the above, the present invention has been described on the basis of the embodiment. However, the present invention is not restricted to this.

For example, it has been described that the repetition patterns 61 are formed on the each chips 65 which is partitioned each other by space. However, the repetition patterns may be formed on a continuous opaque film.

Further, pluralities of kind of pseudo mura defects may be formed on one chip.

Furthermore, it has been described that the light receiver 13 receives scattered light from edge portions of the unit patterns 53 of the repetitive pattern 51 in the photomask 50. Alternatively, the light receiver may receive transmitted light transmitted between the unit patterns 53 of the repetitive pattern 51 of the photomask 50, particularly diffracted light diffracted at edge portions of the unit patterns 53.

In the above, the embodiment has been described in which the member to be inspected is the photomask 50, and the mura defect inspecting apparatus 10 detects the mura defect occurring in the repetitive pattern 51 in the photomask 50 for producing a image device. Alternatively, the member to be inspected may be a image device such as an imaging device or a display device. In the alternative, the mura defect inspecting apparatus 10 may detect the mura defect occurring in a pixel pattern forming an imaging face of an imaging device (specifically, a repetitive pattern forming light receiving portions of a CCD, a CMOS, or the like), or that occurring in a pixel pattern forming a displaying face of a display device (specifically, a repetitive pattern such as thin film transistors, an opposing substrate, or a color filter of a liquid crystal display device).

It has been described that the pseudo mura defects are a CD Mura, a Pitch Mura, a Butting Mura, and a Defect Mura. Alternatively, the pseudo mura defects may be other kinds of pseudo mura defects. The manner of allocating the intensities is not restricted to the embodiment.

While there has been described in connection with the preferred embodiments of the present invention, it will be obvious to those skilled in the art that various changes and modification may be made therein without departing from the present invention, and it is aimed, therefore, to cover in the appended claim all such changes and modifications as fall within the true spirit and scope of the present invention.

What is claimed is:

1. A defect inspection mask comprising a transparent substrate and an opaque film formed on the transparent substrate, wherein the opaque film is patterned to form repetitive patterns regularly arranged in first and second directions on the substrate, each repetitive pattern including a plurality of unit patterns arranged in a regularity, said unit patterns having a pseudo defect so that an intensity of the pseudo defect varies in a stepwise manner among the repetitive patterns in at least one of the first direction based at least on a first parameter and in the second direction based at least on a second parameter, and
wherein said pseudo defect is formed to be detected by a diffraction of light generated at edge portions of the unit patterns.

2. The defect inspection mask according to claim 1 wherein the pseudo defect includes a defect in a critical dimension of the unit patterns, an interval between the unit patterns, positional placements of the unit patterns, or a shape of an individual unit pattern, which defect repeatedly occurs in the repetitive pattern.

3. The defect inspection mask according to claim 2 wherein the intensity of the pseudo defect comprises a variation of widths of the unit patterns.

4. The defect inspection mask according to claim 2 wherein the intensity of the pseudo defect comprises a number of the unit patterns having the defect in critical dimension.

5. The defect inspection mask according to claim 2 wherein the intensity of the pseudo defect comprises the deviation amount in interval between the unit patterns.

6. The defect inspection mask according to claim 2 wherein the intensity of the pseudo defect comprises a number of the unit patterns having the deviation in intervals.

7. The defect inspection mask according to claim 2 wherein the intensity of the pseudo defect comprises the positional displacement amount of the unit patterns.

8. The defect inspection mask according to claim 2 wherein the intensity of the pseudo defect comprises the number of the unit patterns having the positional displacements.

9. The defect inspection mask according to claim 1, wherein the first parameter comprises a variation of widths of the unit patterns, wherein the variation of widths increases in the first direction.

10. The defect inspection mask according to claim 1, wherein the second parameter comprises a number of the unit patterns having the defect in a critical dimension of the unit patterns, and the number of the unit patterns increases in the second direction.

11. The defect inspection mask according to claim 1, wherein the first parameter comprises a deviation amount in an interval between the unit patterns, and the amount of the interval deviation increases in the first direction.

12. The defect inspection mask according to claim 11, wherein the second parameter comprises a number of the unit patterns which are formed having the deviation in intervals, and the number of the unit patterns increases in the second direction.

13. The defect inspection mask according to claim 1, wherein the first parameter comprises an amount of a positional displacement of the unit patterns, and the amount of the positional displacement increases in the first direction.

14. The defect inspection mask according to claim 13, wherein the second parameter comprises a number of the unit patterns which are formed having the positional displacements, and the number increases in the second direction.

15. The defect inspection mask according to claim 1, wherein the first parameter comprises a measure of a variation in shape of the unit patterns, and the variation measure increases in the first direction.

16. The defect inspection mask according to claim 15, wherein the second parameter comprises an interval of the unit patterns which are formed having the shape variation, and the interval decreases in the first and second directions.

17. An apparatus for inspecting a defect occurring in a photomask having a mask repetitive pattern, the mask repetitive pattern having a plurality of mask unit patterns arranged in a first regularity, the apparatus comprising:
a stage to place the photomask;
a light source for irradiating the photomask placed on the stage with light;
a light receiving unit for receiving light diffracted at edge portions of the mask repetitive pattern of the photomask, and
an analyzing unit for analyzing the defect in the mask repetitive pattern based on the received diffracted light,
wherein the apparatus is calibrated by a defect inspection mask,
said defect inspection mask comprises a transparent substrate and an opaque film formed on the transparent substrate,
said opaque film is patterned to form inspection repetitive patterns arranged in a second regularity on the substrate in a first direction and a second direction, each inspection repetitive pattern including a plurality of inspection unit patterns having a pseudo defect so that an intensity of the pseudo defect varies in a stepwise manner among the inspection repetitive patterns in at least one of the first direction based at least on a first parameter and in the second direction based at least on a second parameter, and
said pseudo defect is formed to be detected by a diffraction of light generated at edge portions of the inspection unit patterns.

18. The apparatus of claim 17, wherein the photomask is a photomask for producing an image device.

19. A method for inspecting a defect in a photomask having a mask repetitive pattern, the mask repetitive pattern having a plurality of mask unit patterns arranged in a first regularity, the method comprising:
calibrating a detection sensitivity of an apparatus for inspecting the defect with a defect inspection mask,
placing the photomask on a stage of the apparatus;
irradiating light from a light source of the apparatus onto the photomask to generate diffraction light at edge portions of the mask repetitive pattern,
receiving the diffraction light; and
analyzing the defect based on the received diffraction light,
wherein the defect inspection mask comprises a transparent substrate and an opaque film formed on the transparent substrate,
said opaque film is patterned to form inspection repetitive patterns arranged in a second regularity on the substrate in a first direction and a second direction, each inspection repetitive pattern including a plurality of inspection unit patterns having a pseudo defect so that an intensity of the pseudo defect varies in a stepwise manner among the inspection repetitive patterns in at least one of the first direction based at least on a first parameter and in the second direction based at least on a second parameter, and
said pseudo defect is formed to be detected by the diffraction of light generated at edge portions of the unit patterns.

20. The method of inspecting the defect according to claim 19, wherein the photomask is for producing an image device.

21. A method for manufacturing a photomask having a mask repetitive pattern, the mask repetitive pattern having a plurality of mask unit patterns arranged in a first regularity, the method comprising:
preparing a transparent substrate having an opaque film and a resist film formed thereon,
drawing a predetermined pattern including the repetitive pattern on the resist film by exposure to form a resist pattern,
etching the opaque film using the resist pattern as a mask,
removing the resist pattern to make the photomask, and
carrying out a defect inspection by use of an inspection apparatus,
wherein the inspection apparatus is calibrated by detecting pseudo defects of a defect inspection mask,
said defect inspection mask comprises inspection repetitive patterns arranged in a second regularity on the substrate in first and second directions, each repetitive pattern including a plurality of inspection unit patterns, the inspection unit patterns having a pseudo defect so that an intensity of the pseudo defect varies in a stepwise manner among the inspection repetitive patterns in at least one of the first direction based at least on a first parameter and in the second direction based at least on a second parameter, and
said pseudo defect is formed to be detected by the diffraction of light generated at edge portions of the inspection unit patterns.

22. A method for manufacturing an imaging or display device having a device repetitive pattern being regularly arranged, the method comprising:

carrying out a defect inspection of the device repetitive pattern by use of an inspection apparatus, wherein the inspection apparatus is calibrated so that a detection sensitivity is ascertained or calibrated by detecting pseudo defects of a defect inspection mask, said defect inspection mask comprises inspection repetitive patterns regularly arranged on the substrate in first and second directions, each inspection repetitive pattern including a plurality of inspection unit patterns having a pseudo defect so that an intensity of the pseudo defect varies in a stepwise manner among the inspection repetitive patterns in at least one of the first direction based at least on a first parameter and in the second direction based at least on a second parameter, and said pseudo defect is formed to be detected by the diffraction of light generated at edge portions of the inspection unit patterns.

23. A photomask inspection apparatus calibrator comprising:

a transparent substrate and an opaque film formed on the transparent substrate, wherein the opaque film is patterned to form inspection repetitive patterns regularly arranged on the substrate in first and second directions, each inspection repetitive pattern including a plurality of inspection unit patterns having a pseudo defect so that an intensity of the pseudo defect varies in a stepwise manner among the inspection repetitive patterns in at least one of the first direction based at least on a first parameter and in the second direction based at least on a second parameter, and said pseudo defect is formed to be detected by the diffraction of light generated at edge portions of the inspection unit patterns.

* * * * *